United States Patent [19]

Grund

[11] Patent Number: 5,334,773
[45] Date of Patent: Aug. 2, 1994

[54] MICROBIAL PRODUCTION OF CIS-DIHYDRODIOL AND PHENOL DERIVATIVES OF BENZOCYCLOBUTENE

[75] Inventor: Alan D. Grund, Manitowoc, Wis.

[73] Assignee: Bio-Technical Resources, L.P., Manitowoc, Wis.

[21] Appl. No.: 78,670

[22] Filed: Jun. 16, 1993

Related U.S. Application Data

[63] Continuation-in-part of Ser. No. 785,978, Oct. 31, 1991, abandoned.

[51] Int. Cl.$^5$ ............... C07C 39/12; C07C 39/17
[52] U.S. Cl. ............... 568/734; 568/716; 568/731; 568/732; 568/763
[58] Field of Search ............... 568/734, 732, 716, 763, 568/737, 731

[56] References Cited

U.S. PATENT DOCUMENTS

| | | | |
|---|---|---|---|
| 4,174,460 | 11/1979 | Seifert et al. | 568/763 |
| 4,508,822 | 4/1985 | Taylor | 435/155 |
| 4,520,103 | 5/1985 | Ensley Jr. | 435/155 |
| 5,120,884 | 6/1992 | Thomas | 568/734 |
| 5,227,536 | 7/1993 | Thomas et al. | 568/734 |

OTHER PUBLICATIONS

Bryd et al. "Chemical Abstract" vol. 115 (21) Nov. 1991 115:227999z.

Thomas, et al "Chemical Abstracts" vol. 117 (3) Jul. 1992 117:26032w.

Thomas et al "Chemical Abstracts" vol. 117(19) Nov. 1992 117:191464.

*Primary Examiner*—Werren B. Lone

[57] ABSTRACT

A process for microbial conversion of benzocyclobutene to the corresponding 3,4-dihydrodiol followed by acid catalyzed dehydration to 4-hydroxybenzocyclobutene.

1 Claim, No Drawings

MICROBIAL PRODUCTION OF CIS-DIHYDRODIOL AND PHENOL DERIVATIVES OF BENZOCYCLOBUTENE

CROSS-REFERENCE TO RELATED APPLICATION

This application is a continuation-in-part of U.S. Ser. No. 07/785,978 filed Oct. 31, 1991 now abandoned.

BACKGROUND OF THE INVENTION

1. Field of the Invention

The present invention relates to the bioconversion of benzocyclobutene (BCB) to the 3,4-cis-dihydrodiol compound and the subsequent acid-catalyzed dehydration to form the 4-hydroxybenzocyclobutene compound. These novel compounds have utility as intermediates for the production of polymers.

2. Description of the Related Art

Formation of cis-dihydrodiols from various aromatic hydrocarbons by bacteria has been described by D. T. Gibson et al., *Biochemistry*, Vol. 9, No. 7, 1973, p. 1626+ and p. 1631+, and Vol. 12, No. 8, 1973, p. 1520+. A cis-dihydrodiol intermediate has been found to be a common metabolite in the bacterial degradation of a variety of aromatic hydrocarbons, including benzene, toluene, naphthalene, biphenyl, ethylbenzene, benzoic acid, phthalic acid, anthracene and phenanthrene. U.S. Pat. No. 4,508,822 discloses the preparation of dihydrodiols of the general formula:

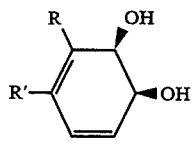

where R and R' are substituents which may be the same or different, such as halogen, alkyl and the like. Generally, such dihydrodiols are of the 2,3-dihydrodiol configuration. That is, the hydroxy groups are introduced directly adjacent to the ring substituent R. The only known exception to this general rule is the 4,5-dihydrodiol formed by some bacteria in the degradation of phthalic acid.

U.S. Pat. No. 4,520,103 describes the formation of the 2,3-dihydrodiol of indole as an intermediate in the production of indigo.

SUMMARY OF THE INVENTION

The present invention relates to the formation of a dihydrodiol resulting from bacterial bioconversion of the aromatic hydrocarbon benzocyclobutene. Mutant strains of Rhodococcus organisms capable of converting benzocyclobutene to the 3,4-dihydrodiol have been developed. The growth of the mutant strain in the presence of benzocyclobutene results in the production of the 3,4-dihydrodiol intermediate of benzocyclobutene. Acid-catalyzed dehydration of the 3,4-dihydrodiol compound results in formation of 4-hydroxybenzocyclobutene. The corresponding sequential reactions are outlined below.

4-Hydroxybenzocyclobutene

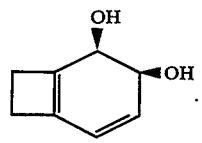

3,4-Dihydrodiol       4-Hydrozybenzocyclobutene

DESCRIPTION OF THE PREFERRED EMBODIMENTS

Organisms capable of growth on a variety of aromatic hydrocarbons such as benzene, toluene, ethylbenzene and o-xylene were isolated from the environment by selective culture. Certain of the resulting isolates were found to partially metabolize benzocyclobutene to a mixture of dead-end metabolites, but were not able to grow on benzocyclobutene. Mutants lacking a functional diol dehydrogenase were obtained by mutagenesis with N-methyl-N-nitro-N-nitrosoguanidine, followed by ampicillin/cycloserine enrichments for mutants unable to grow on toluene. Diol dehydrogenase deficient mutants were identified by the accumulation of dihydrodiols upon exposure to various aromatic hydrocarbons.

The mutant, 75-2, derived from a Rhodococcus isolate 75 WT, converts benzocyclobutene to the corresponding 3,4-dihydrodiol compound. The dihydrodiol at a concentration of 200 to 4,000 parts per million in aqueous solution is dehydrated by addition of a mineral acid such as hydrochloric acid or sulfuric acid to a concentration of 0.1N to 8N, preferably 1.0 to 5N, at a temperature of 20° to 50° C. for 15 minutes to 20 hours, preferably 1 to 10 hours. The resulting phenols can be recovered such as by extraction with water immiscible, polar organic solvents, such as ethyl acetate, methyl ethyl ketone, or the like. Generally over 95% of the recovered phenols are 4-hydroxybenzocyclobutene with the balance 3-hydroxybenzocyclobutene.

EXAMPLE

Rhodococcus strain 75-2 American Type Culture Collection (ATCC) 55201 is grown in baffled 125 ml Erlenmeyer flasks on a minimal salts medium with succinate at 1.0 wt %. Benzocyclobutene is supplied as a vapor to the culture. After 24 hours incubation on a rotary shaker at 150 rpm and 30° C., the culture is acidified with HCl to a concentration of 1.0N, and held at room temperature for 4 hours. The broth is then extracted with an equal volume of ethyl acetate and analyzed for phenols by gas chromatography. The 4-hydroxybenzocyclobutene was present at 235 ppm, the 3-hydroxybenzocyclobutene at 7 ppm.

I claim:

1. A dihydrodiol of the formula

* * * * *